United States Patent

Janjic

[11] 3,934,348
[45] Jan. 27, 1976

[54] METHOD OF FORMING A PORCELAIN CROWN

[76] Inventor: Bora Janjic, 541 Lincoln Road, Miami Beach, Fla. 33139

[22] Filed: Jan. 2, 1975

[21] Appl. No.: 537,967

[52] U.S. Cl. ..................................... 32/12
[51] Int. Cl.² .................................... A61C 5/08
[58] Field of Search ..................... 32/12, 8, 13, 2

[56] References Cited
UNITED STATES PATENTS

| | | | |
|---|---|---|---|
| 2,194,790 | 3/1940 | Gluck | 32/12 |
| 2,980,998 | 4/1961 | Coleman et al. | 32/12 |
| 3,413,723 | 12/1968 | Wagner et al. | 32/8 |
| 3,481,772 | 12/1969 | MacNairn et al. | 32/12 X |
| 3,761,728 | 9/1973 | Kochavi | 32/12 |

Primary Examiner—Louis G. Mancene
Assistant Examiner—J. Q. Lever
Attorney, Agent, or Firm—Blair & Brown

[57] ABSTRACT

A method of forming a porcelain crown that requires no shoulder, and can be fitted over any type of standard impression made by a dentist. In the method, a laboratory plaster model is made from a dentist's impression and includes male and female dies. The male die has successive layers of materials applied thereupon comprising first a 0.002 gauge platinum film followed successively by a first layer of gold crust, a second layer of gold crust and opaque porcelain, upon which a regular porcelain is applied that fits the female die with the regular porcelain receiving thereafter a final application of glazing powder. The crown is baked between each step of the process.

6 Claims, 10 Drawing Figures

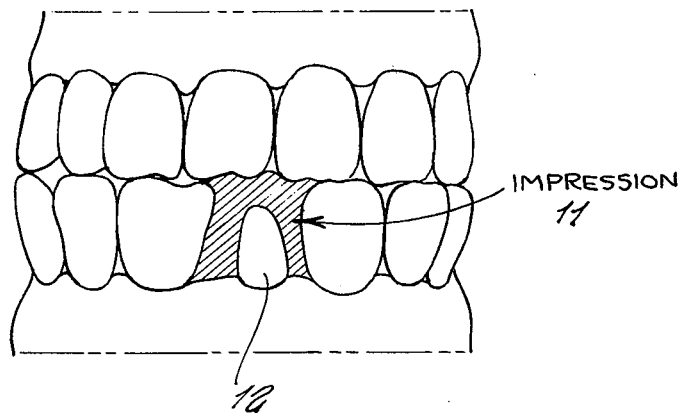
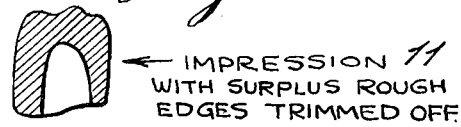
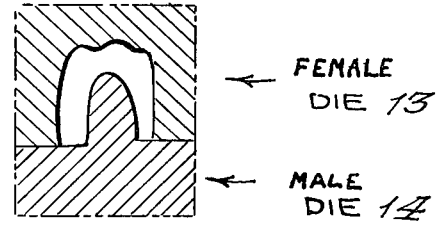
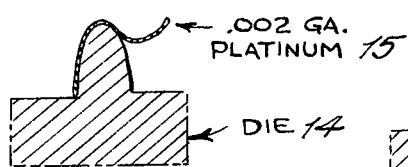
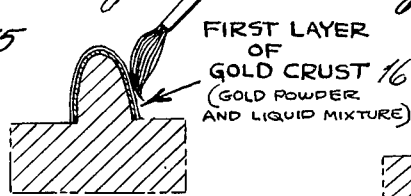
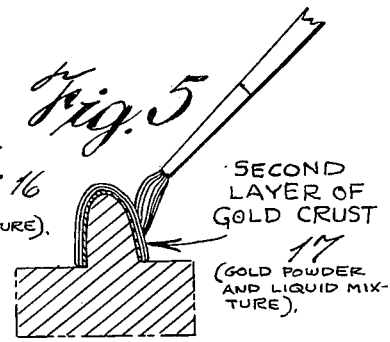
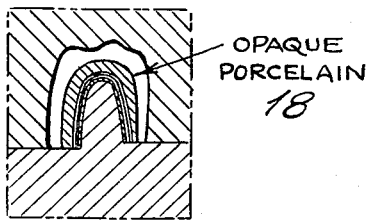
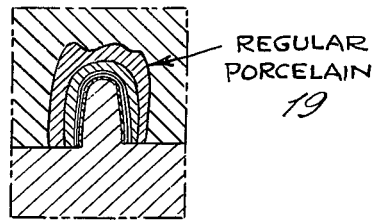
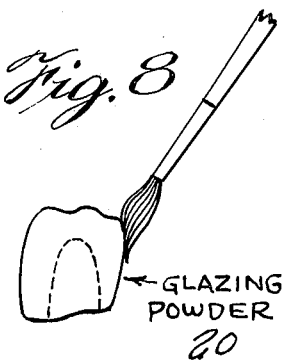
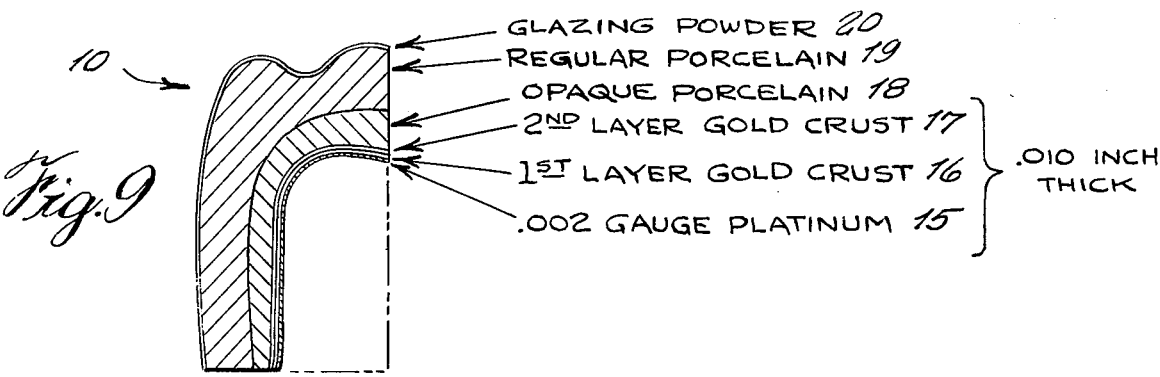

METHOD OF FORMING A PORCELAIN CROWN

This invention relates to a process for the making of a porcelain crown.

A principal object of the present invention is to provide an improved method of forming a porcelain crown which can be fitted over any type of impression that is made by the dentist from all sizes and types of teeth.

Another object is to provide a method of forming an improved porcelain crown that does not require a dentist to grind down the tooth in the patient's mouth, to produce a shoulder, such as is necessary for other crowns to rest upon, but instead a crown is made from successive layers of 0.002 gauge platinum film, gold crust, opaque porcelain, and glazing powder to fit over a tooth requiring a crown.

These and other objects will be readily evident upon a study of the following specification and the accompanying drawing, wherein:

FIGS. 1 through 8 are diagrammatic views showing subsequent steps in the method of forming the porcelain crown of the present invention.

FIG. 9 is a fragmentary cross-sectional view of the completed porcelain crown.

Referring to the drawing in detail, the reference numeral 10 represents a porcelain crown produced by following the method according to the present invention.

First, as shown in FIG. 1, a dentist makes an impression 11 around the tooth 12 that is to be crowned. Rough edges on the impression are ground off and rounded, as shown in FIG. 1a. The dentist's impression is then sent to a laboratory which makes a model for a crown. For each tooth, a female die 13 and a male die 14 are made of the model from a hard dental plaster.

Platinum film 15 of 0.002 inch gauge is fitted over the die 14 so to conform to the die shape.

A first layer of gold crust 16 is then applied over the platinum with a small brush and allowed to dry. This is now placed in a porcelain furnace and baked in air until the temperature reaches 1950°F. It is then removed from the furnace and allowed to cool.

A second coat of gold crust 17 is then applied, and the device is again place into the porcelain furnace and baked in air until the temperature reaches 1850°F. The thickness of the crown is now 0.010 inch.

Opaque porcelain 18 is now applied on the crown by a brush and is baked in the porcelain furnace in air starting with a temperature of 800°F. continuing until it reaches 1200°F. It is then baked in a vacuum from 1200°F. until it reaches 1750°F. The vacuum is then released, and the crown is then baked in air to 1825°F. The crown is then allowed to cool.

Regular porcelain 19 is now applied in sufficient quantity to shape the crown to the die 13 contour, and the crown is then again placed into the porcelain furnace and baked in air beginning at 800°F. and increasing to 1200°F. It is then baked in a vacuum beginning at 1200°F. and increasing to 1650°F. The vacuum is then released, and the crown is then baked in air increasing to 1700°F. The crown is then allowed to cool.

A glazing powder 20 is then applied to the crown with a brush. The crown is placed in the porcelain furnace and baked in air beginning at 800°F. and increasing to between 1710° to 1720°F. It is then allowed to cool, thus completing the crown construction.

From the above description of the method of making the porcelain crown of the present invention it is clear that the crown can be made to fit all teeth, of all sizes and shapes, and without the need to grind down the tooth until there is a shoulder for the crown to reat upon. The dentist takes an impression of the tooth needing a crown, and a laboratory plaster model is made from the impression and includes male and female dies. On the male die are laid and baked successive layers of 0.002 gauge platinum film, gold crust, opaque porcelain, and a final application of glazing powder. The hollow portion of the new crown naturally is a perfect reproduction of the tooth it is to fit over because the die employed to build the crown is made from an impression of the tooth. The crown, therefore, is a perfect fit for the tooth, and additionally, should the tooth need a broader grinding surface to mate with others it works against and with, then the regular porcelain layer can be made thicker and broader to provide the needed substantially horizontal surface, such as shown in FIGS. 7, 8, and 9.

Having thus described the preferred embodiments of the invention it should be understood that numerous structural modifications and adaptations may be resorted to without departing from the spirit of the invention.

What is claimed is:

1. A method for forming a dental crown on a crown model made from a dentist's impression, including the steps of forming male and female dies on the model in hard dental plaster, applying a 0.002 inch gauge platinum film to the male die in form fitting relation, brushing a layer of gold crust on the platinum film, baking the crown, brushing a second layer of gold crust on the crown, baking the crown, applying a regular porcelain to the crown conformed to the contour of the female die, baking the crown, brushing a glazing powder on the crown, and finally baking the crown.

2. The method as set forth in claim 1, wherein the baking step after applying the first layer of gold crust consists of baking in a porcelain furnace in air up to 1950°F.

3. The method as set forth in claim 2, wherein the baking step after applying the second layer of gold crust consists of baking in the furnace in air to 1850°F.

4. The method as set forth in claim 3 wherein the baking step after applying the opaque porcelain consists of baking in the furnace in air starting with a temperature of 800°F. then increasing to 1200°F., and then bake in the furnace in a vacuum starting with a temperature of 1200°F. then increasing to 1750°F., release the vacuum and continue to bake in air to a final temperature of 1825°F.

5. The method as set forth in claim 4, wherein the baking step after applying the regular porcelain consists of baking in the furnace in air beginning with a temperature of 800°F. and increasing to 1200°F., and then bake in the furnace in a vacuum beginning with a temperature of 1200°F. and increasing to 1650°F., release the vacuum and continue to bake in air to a final temperature of 1700°F.

6. The method as set forth in claim 5, wherein the baking step after applying the glazing powder consists of baking in the furnace in air beginning with a temperature of 800°F. and increasing to between 1710° and 1720°F.

* * * * *